United States Patent [19]
Beck et al.

[11] Patent Number: 5,846,217
[45] Date of Patent: Dec. 8, 1998

[54] IONTOPHORETIC BIOELECTRODE AND METHOD OF USING SAME

[75] Inventors: Jon E. Beck, Salt Lake City; Ralph Karl Koschinsky, Sandy, both of Utah

[73] Assignee: Iomed, Inc., Salt Lake City, Utah

[21] Appl. No.: 902,251

[22] Filed: Jul. 29, 1997

[51] Int. Cl.⁶ .............................. A61N 1/30; A61N 1/04
[52] U.S. Cl. ............................................ 604/20; 607/152
[58] Field of Search ................... 604/20, 890.1; 602/47, 48, 58; 128/114.1; 607/152, 153

[56] References Cited

U.S. PATENT DOCUMENTS

| | | | |
|---|---|---|---|
| 1,862,122 | 6/1932 | Schrader . | |
| 2,807,262 | 9/1957 | Lew . | |
| 4,177,817 | 12/1979 | Bevilacqua | 128/152 |
| 4,362,165 | 12/1982 | Carmon et al. | 128/640 |
| 4,867,166 | 9/1989 | Axelgaard et al. | 128/640 |
| 4,917,688 | 4/1990 | Nelson et al. | 604/892.1 |
| 5,064,422 | 11/1991 | Wick | 604/307 |
| 5,084,006 | 1/1992 | Lew et al. | 604/20 |
| 5,087,241 | 2/1992 | Mathiesen et al. | 604/20 |
| 5,087,242 | 2/1992 | Petelenz et al. | 604/20 |
| 5,158,537 | 10/1992 | Haak et al. | 604/20 |
| 5,236,412 | 8/1993 | Lloyd et al. | 604/20 |
| 5,320,597 | 6/1994 | Sage, Jr. et al. | 604/20 |
| 5,328,455 | 7/1994 | Lloyd et al. | 604/20 |
| 5,385,543 | 1/1995 | Haak et al. | 604/20 |
| 5,450,845 | 9/1995 | Axelgaard | 604/20 |
| 5,558,632 | 9/1996 | Lloyd et al. | 604/20 |

FOREIGN PATENT DOCUMENTS

| | | | |
|---|---|---|---|
| WO 92/07619 | 5/1992 | WIPO | 604/20 |
| WO 92/10235 | 6/1992 | WIPO | 604/20 |
| WO 94/22528 | 10/1994 | WIPO | 604/20 |

*Primary Examiner*—Wynn Wood Coggins
*Assistant Examiner*—Sharon Finkel
*Attorney, Agent, or Firm*—Workman, Nydegger & Seeley

[57] ABSTRACT

An improved iontophoretic bioelectrode constructed with a novel access window that conveniently allows a clinician direct access to the drug reservoir without prematurely exposing the adhesive layer. The access window is a partial cut out or perforation of a release liner that, when opened, only reveals the drug reservoir to the clinician while the remainder of the release liner simultaneously remains protectively covering the adhesive layer.

15 Claims, 4 Drawing Sheets

IONTOPHORETIC BIOELECTRODE AND METHOD OF USING SAME

BACKGROUND OF THE INVENTION

1. The Field of the Invention

The present invention relates generally to bioelectrodes and their methods of use in iontophoresis therapy. More specifically the present invention relates to an improved iontophoretic bioelectrode having a novel construction that allows for efficacious application of an ionic solution prior to use and to a method of using same.

2. The Relevant Technology

Novel methods of medicament delivery are continually being sought which are less invasive and more efficient than conventional delivery methods. For example, conventional hypodermic injection commonly entails pain and risk of infection. Oral ingestion entails absorption of the medicament from the digestive tract after the blood containing the medicament "first passes" through the liver. As a result, much of an orally ingested drug may be metabolically inactivated and removed from the blood stream by the first pass effect of the liver before the medicament has had an opportunity to exert its pharmacological effect on the target tissue area. Local delivery of medicaments, therefore, presents advantages over oral administration, an application characterized by inefficiency and unpredictability, and over hypodermic injection, an invasive, inconvenient, and sometimes risky technique.

One local delivery method, known as iontophoresis, is a safe, effective, non-invasive, and relatively painless medicament delivery method that delivers an ionic form of a drug through the skin or tissue of a patient, or animal, in the presence of an electrical potential. Iontophoresis is typically performed by placing a first "active" bioelectrode containing an ionic drug solution in contact with the skin, at a location where the drug is to be introduced into the patient's bloodstream. A second "inactive" bioelectrode filled with a non-toxic electrolytic solution or substance is placed in close proximity to the first bioelectrode so that as DC power is supplied, electrical current passes through the skin thereby completing an electrical circuit between the electrodes. Then, as current flows, ionized drug molecules non-invasively and effectively migrate from the active electrode into the tissues and bloodstream of the patient. In their most basic form, conventional bioelectrodes include a conductive element for enabling an electric field to be produced, a reservoir element for holding the electrolytic solution or ionic drug, a means for securing the conductive element to the reservoir element and a means for securing the entire bioelectrode to the patient, usually an adhesive.

Generally, bioelectrodes can be divided into two categories. The first is a pre-filled type, wherein the manufacturers send clinicians bioelectrodes that are prepackaged with the electrolyte or drug solution already contained in the reservoir element. The second type, known as "dry-state" or "hydratable" electrodes, utilize reservoirs that are customarily filled with liquid electrolytes or drug solutions immediately prior to use, either before or after their application to the patient. Yet both categories have numerous difficulties which make their use inconvenient and problematic.

For example, with respect to the prepackaged or pre-filled devices, many drugs have poor stability when stored in solution and the shelf life of a pre-filled iontophoretic drug solution is unacceptably short for various medical reasons. Leakage from the reservoir and corrosion of the electrodes and other electrical components may also occur. In addition, pre-filled devices are often difficult to apply because the protective seal, which covers the electrode opening and retains the fluid within the reservoir, must be removed prior to application on the skin and, after removal, the contents of the reservoir often spill when attempting to secure the electrode to the patient.

With respect to the dry-state devices a further distinction exists between electrode devices depending upon the particular type of reservoir element that is used and examples thereof can be found by reference to U.S. Pat. Nos. 5,328,455 and 5,558,632, both disclosures of which are herein expressly incorporated by reference. While both patents describe very effective bioelectrodes, the electrodes suffer from difficulty and/or inconveniences as outlined below.

For example, "direct fill" or "direct application" devices typically have a release liner that must be removed to expose the reservoir element in order that a clinician might be able to fill the reservoir with an appropriate amount of drug solution. The root of the problem, however, lies with the fact that removal of the release liner also exposes the adhesive at a time before the clinician is ready to secure the bioelectrode to the patient.

Long term exposure of the adhesive sometimes compromises the integrity of the adhesive due to adhesive drying during the time delay between exposure of the adhesive, filling of the reservoir and application of the bioelectrode to the patient, as sometimes occurs when the adhesive sits exposed for several hours before use. In addition, the time delay also affords opportunity for airborne contaminants such as dust, pollen, hair, lint and other related particles to adhere to the adhesive thereby reducing its effectiveness.

A further disadvantage is that, during filling of the reservoir, drug solution may be spilled over onto the prematurely exposed adhesive surface thereby contaminating it and eliminating or diminishing the adherent qualities of the adhesive.

Even further, a prematurely exposed adhesive increases the likelihood of the adhesive "folding over" onto itself or having a foreign object being inadvertently set upon the adhesive and adhering itself thereto. In particular, such foreign objects include the fingers and hands of clinicians during their handling of the bioelectrode which, in order to avoid complications, unnecessarily demands improved clinician dexterity.

One conventional method attempting to minimize the problems associated with direct fill electrodes are "tray fill" electrodes, another type of dry-state electrode. The problems are minimized by tray fill electrodes because an access hole allows a clinician to introduce solution to the reservoir element without prematurely exposing the adhesive.

Tray fill bioelectrodes, however, particularly suffer other problems such as an unavoidable time lapse between the time the drug solution is injected into the tray and the time the hydratable element absorbs the drug solution. This creates an inconvenient waiting period before treatment can begin.

In addition, since the tray itself is often a rigid plastic and not a flexible sheet, as with most direct fill electrodes, removal of the release liner frequently causes spillage of the drug solution.

Yet even further tray-fill problems occur when the hydratable element does not "wick up" the entire fluid volume of drug solution. For example, poor reservoir hydration and leakage occur, since it is well known that bioelectrodes that do not hold drug solution or fluid well, often leak.

A unique and concomitant set of problems arises with yet another type of tray fill bioelectrodes that have their reservoir elements filled after the bioelectrode is applied to the patient. The salient problem with this type is that whoever fills the bioelectrode has no accurate means by which to evaluate whether the hydratable reservoir has been over or under filled because drug solution is not directly added to the reservoir but is indirectly added through a series of holes away from the hydratable element. With all tray fill systems, material and labor costs are high due to the placement and manufacture of the tray.

SUMMARY AND OBJECTS OF THE INVENTION

It is therefore a primary object of the present invention to provide a new and improved method and apparatus for iontophoretic delivery of drugs that provides easy and convenient access to the reservoir element without prematurely exposing the adhesive.

It is another object of the present invention to provide a new and improved method and apparatus for iontophoretic delivery of drugs that protects the integrity of the adhesive until ready to use.

It is still another object of the present invention to provide a new and improved method and apparatus for iontophoretic delivery of drugs that keeps the adhesive surface from being inadvertently wetted during the filling of the drug reservoir.

It is yet another object of the present invention to provide a new and improved method and apparatus for iontophoretic delivery of drugs that prevents the adhesive from drying out prior to the time of use.

Still yet another object of the present invention is to provide a new and improved method and apparatus for iontophoretic delivery of drugs that allows for a cleaner and more aseptic medical technique during clinician handling.

Still an even further object of the present invention is to provide a new and improved method and apparatus for iontophoretic delivery of drugs that allows for easier handling by the clinician.

In accordance with the invention as embodied and broadly described herein, the foregoing and other objectives are achieved by providing an improved iontophoretic bioelectrode constructed with a novel access window that conveniently allows a clinician direct access to the drug reservoir without prematurely exposing the adhesive layer. The access window is a partial cut out or perforation of a release liner that, when opened, reveals the drug reservoir to the clinician while the remainder of the release liner simultaneously remains protectively covering the adhesive layer.

These and other objects and features of the present invention will become more fully apparent from the following description and appended claims, or may be learned by the practice of the invention as set forth hereinafter.

BRIEF DESCRIPTION OF THE DRAWINGS

In order to more fully understand the manner in which the above-recited and other advantages and objects of the invention are obtained, a more particular description of the invention will be rendered by reference to a specific embodiment thereof which is illustrated in the appended drawings. Understanding that these drawings depict only typical embodiments of the invention and are not therefore to be considered to be limiting of its scope, the invention in its presently understood best mode for making and using the same will be described and explained with additional specificity and detail through the use of the accompanying drawings in which.

DETAILED DESCRIPTION OF THE PREFERRED EMBODIMENTS

The present invention relates to a novel access window in a bioelectrode that allows the addition of drug solution to a suitable drug reservoir in order to iontophoretically deliver the solution to a patient while simultaneously increasing convenience to the clinician and preserving adhesive integrity of the adhesive layer until such time as the bioelectrode is readied for use.

Figure 1:
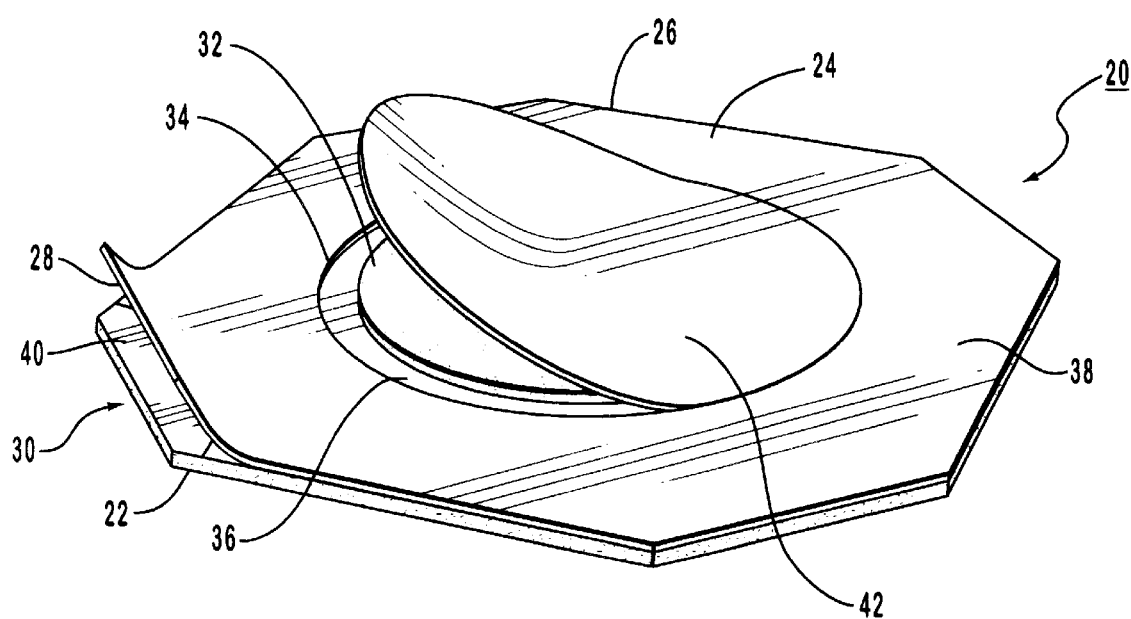
FIG. 1 is a perspective view of an improved direct fill iontophoretic bioelectrode according to a preferred embodiment of the present invention.

With reference to FIG. 1, a bioelectrode configured for delivering ions of an ionic solution is depicted generally as 20. The bioelectrode 20 is typically configured for an iontophoretic drug delivery method, as described in the background section, in cooperation with a second, typically inactive electrode, and a D.C. power source connected across both electrodes. Although the inactive electrode is typically a Karaya gel electrode, it should be understood that two bioelectrodes 20 according to the present invention could also effectively be used for both the active and inactive electrodes or for two active electrodes used to administer drug solutions having opposite ionic charges. When the bioelectrode 20 is, in fact, the active electrode, the solution is typically an ionic drug solution suitable for iontophoretic delivery and when utilized as the inactive or "dispersive" electrode, the solution, or substance, is typically a non-toxic electrolytic solution useful in facilitating electrical current. Two of the most common drug solutions used are dexamethasone sodium phosphate and lidocaine hydrochloride. Dexamethasone sodium phosphate is a useful drug for the local treatment of local inflammation, tendinitis, bursitis, arthritis or carpal tunnel syndrome and lidocaine hydrochloride is useful for local anesthesia.

The bioelectrode 20 has a substrate 22 that is often constructed as a soft, flexible polymer sheet in order to increase patient comfort and to act as a sealant by conforming to numerous and varied patient application surfaces. Since the substrate 22 comes into direct contact with the skin of a patient and potentially the skin of the clinician, the substrate 22 has additional other criteria that should be considered when selection as to the type of material is made. Some of the more salient considerations include toxicity and irritants. The substrate 22 may alternatively be a thin film or other material.

The substrate 22 is constructed by techniques well known to those skilled in the art in such a manner that the front side 24 is essentially a non-adhesive layer with a peripheral, outer region 26 having an adhesive layer 28 applied thereon. The back side 30 of substrate 22 is preferably fabricated with a material having non-stick properties that allows for practical handling of the bioelectrode 20.

Mounted in the center of the front side 24 is a fluid reservoir 32, typically a hydratable element that is hydrated with an appropriate solution by a clinician at the time of use of the bioelectrode 20. As described previously, the particular solution applied depends upon whether the bioelectrode 20 is the active or inactive electrode.

Various hydratable elements might be used to construct the fluid reservoir 32 and since, like the substrate 22, the fluid reservoir 32 comes into contact with the skin of a patient, salient construction considerations also include toxicity and irritants. Some of the more useful materials used in construction include reticulated materials such as polyurethane foam or fibrous mats or fabrics, such as matted rayon. Particular preferred materials include: SIFZ Felted foam #2 obtainable from Foamex, Inc.; Crest Felted S-90; Z, firmness 2 distributed by Great Western; PVA foam E-1 or E-2 distributed by Rippey Corp.; or Hypol foam (2002, 2000 or 3000) produced by Hampshire Chemical Inc.

It should be pointed out that while the fluid reservoir 32 is mounted on the same side of substrate 22 as the adhesive layer 28, the adhesive layer 28 is cooperatively mounted about the circumference 34 of the fluid reservoir 32 such that in the area of the fluid reservoir 32, the substrate 22 does not contain any adhesive properties. Further isolating the circumference 34 of the fluid reservoir 32 from the adhesive layer 28 is a non-adhesive gap 36. It is possible, however, that on the front side 24 beneath the fluid reservoir 32 there are materials that contain adhesive properties but merely do so for the purposes of adhering the fluid reservoir 32 thereto during fabrication. But once fabrication of the bioelectrode 20 is complete, adhesive properties are no longer exposed.

Attached to the front side 24 of the substrate 22 is a release liner 38 that protectively covers the adhesive layer 28 and the fluid reservoir 32 until the bioelectrode 20 is readied for use. The release liner 38 is coated with and contains chemical release agents that allow the release liner 38 to stick to the adhesive layer 28 without becoming permanently attached thereto and while simultaneously avoiding detrimental destruction of the adhesive qualities contained within the adhesive layer 28. The chemical release agents and the construction techniques of the release liner 38 are well known to those skilled in the art and are not further described herein in detail. The release liner 38 may additionally have manufactured therein a peel tab 40 in order to facilitate removal of the release liner 38 during use of the bioelectrode 20.

Defined on a portion of the release liner 38 covering the fluid reservoir 32, as a partial carve out or cut out, is an access window 42 that provides easy access to the fluid reservoir 32. It should be appreciated by those skilled in the art that the access window 42 partially cut out of the release liner 38 reveals, either in complete or partial exposure, the fluid reservoir 32 while simultaneously protectively covering adhesive layer 28. The amount of exposure provided by the access window 42 is a function of both the type of cut employed in the release liner 38 and the preference of the clinician utilizing the bioelectrode 20. The types of cuts available are well known to those skilled in the art but are preferably a scrim-die cut or a perforated cut. The preference of the clinician utilizing the bioelectrode 20 becomes a factor for determining the amount of exposure of the fluid reservoir 32 because the clinician is free to bend back the access window 42 as much or as little as necessary in order to effectively hydrate the fluid reservoir 32 with the appropriate solution.

Figure 2:
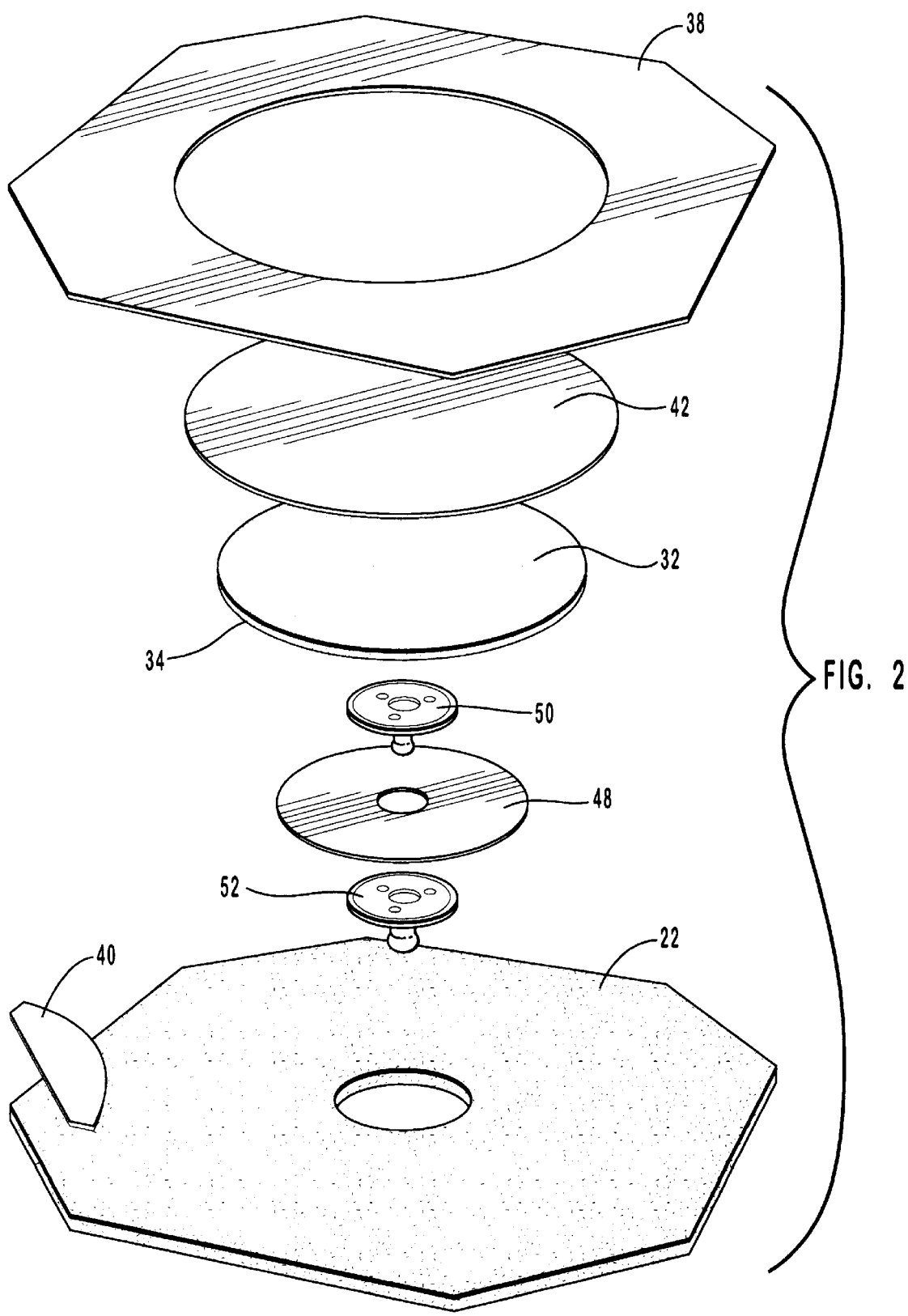
FIG. 2 is an exploded side view of the iontophoretic bioelectrode of FIG. 1.
Figure 3:
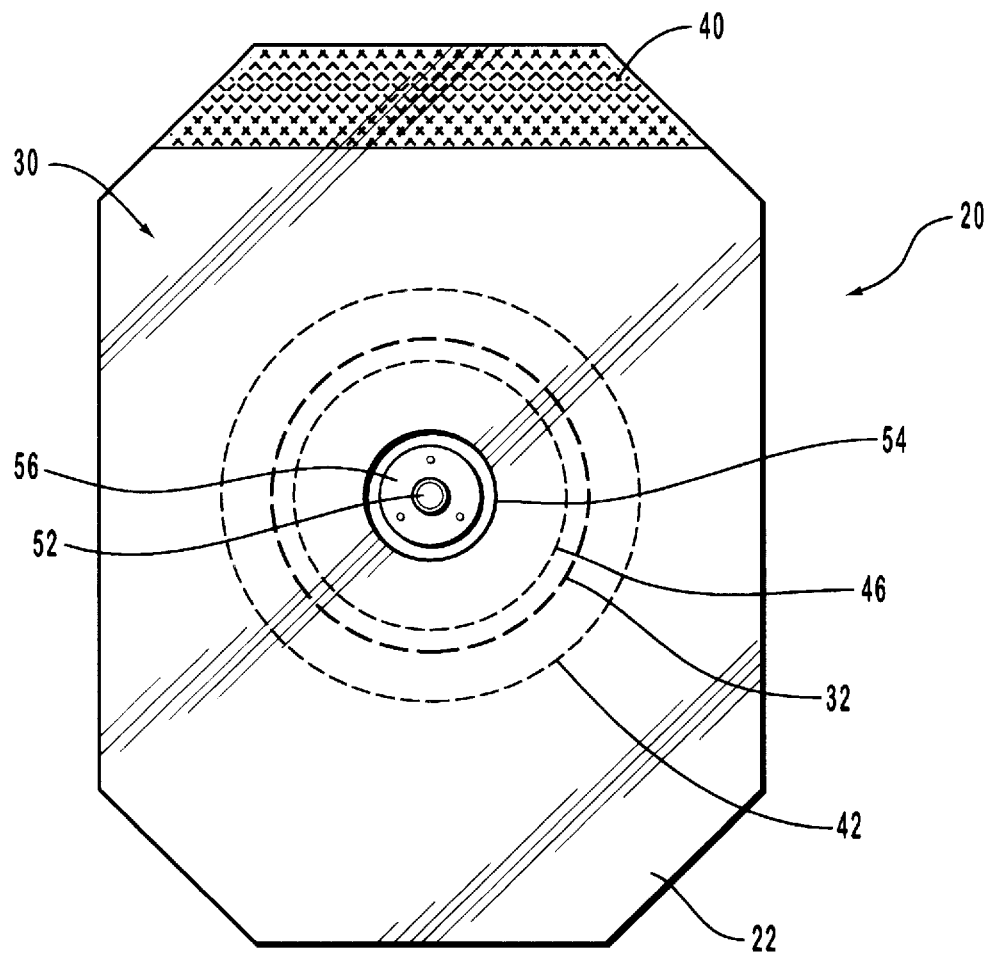
FIG. 3 is a back side, plan view of the iontophoretic bioelectrode of FIG. 1.

Further elements not readily ascertainable from the previous description are also constructed into the bioelectrode 20 and are now described with particular reference to FIGS. 2 and 3. A conductive element 48 is associated with the fluid reservoir 32 in order that an electric current might be established during the iontophoretic application after being connected to a suitable power source (not shown). The conductive element 48 is typically adjacent the fluid reservoir 32 so that drug molecules can effectively migrate from the fluid reservoir into the patient's bloodstream. Facilitating connection of the conductive element 48 to the power source are a snap stud 50 and a snap eyelet 52 mounted in cooperating fashion on opposite sides of the conductive element 48. Joinder of the snap stud 50 and the snap eyelet 52 about the conductive element 48 are well known within their art and are also not described herein.

In order that the conductive element 48 by way of the snap eyelet 52 are readily available to be connected to the suitable power source, an appropriate sized hole 54 is manufactured into the back side 30 of the substrate 22 to reveal the snap eyelet 52 and accompanying metallic border 56.

Figure 4:
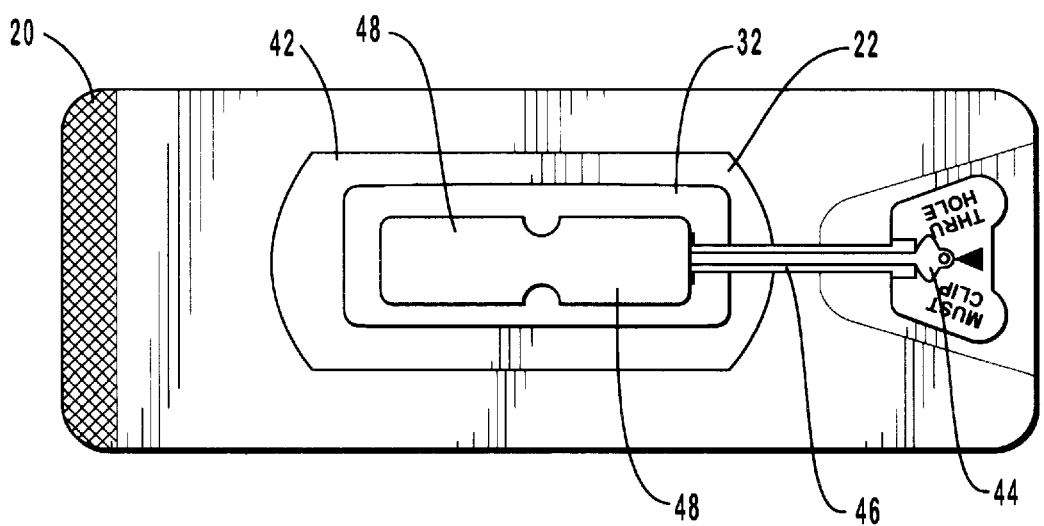
FIG. 4 is a back side, plan view of an iontophoretic bioelectrode according to an alternate embodiment of the present invention.

Another preferred embodiment of the bioelectrode 20 is depicted in FIG. 4. The primary differences being the substantially rectangular shape of the bioelectrode 20, fluid reservoir 32 and access window 42 and the design of the conductive element 48 which is now substantially coextensive with the fluid reservoir 32. A secondary difference illustrated is that the means depicted to assist the conductive element 48 in attachment to the power source is now an opening 44 near the end of the extension member 46.

It should be appreciated that the conductive element 48 is even further adaptable in design in order to accommodate the actual fluid reservoir used. Such design will not only entail considerations relating to an appropriate physical arrangement but will entail a means by which electric current density can be controlled over the entire face of the fluid reservoir. Often times the conductive element 48 is simply a current-conducive solution evenly distributed over a flexible polymer material thereby facilitating even distribution of electric current during the iontophoretic process.

An even, or uniform, distribution of current is essential during the iontophoretic process in order to evenly distribute ions into the target tissue area and to prevent potential hot, or burn, spots that are associated with uneven, non-uniform current distribution. Further assisting in the uniform current distribution is substrate 22. As can best be seen in FIG. 2, the substrate 22, to which the fluid reservoir 32 is ultimately mounted, is significantly extended beyond the circumference 34 of the fluid reservoir 32 thus providing uniform securement of the fluid reservoir 32 on the patient's skin and in turn uniform current distribution.

It should be appreciated that what has heretofore been described should not be construed as limiting but merely as representative. It is to be understood that the bioelectrode 20, while having been described with an access window 42 of substantially circular or rectangular shape, may be advantageously altered to accommodate various other conveniently shaped and sized fluid reservoirs. No matter what ultimate shape the fluid reservoir takes, what remains important is that the access window 42 remain in a protectively covering position in substantial alignment over the fluid reservoir in a manner that does not reveal or expose substantial amounts of adhesive layer 28 during the opening of the access window 42 or during the addition of the solution to the reservoir.

Even further contemplated are prepackaged or pre-filled bioelectrodes, not previously described herein in detail, that are distributed directly to clinicians with access windows already cut in the release liner. While the prepackaged electrodes do not require filling of the fluid reservoirs before use, the access windows would provide for convenient visual monitoring of fluid levels and/or the types of fluids used therein, i.e. based upon different colored drug solutions.

As previously described, a conventional prior art bioelectrode has the fluid reservoir of the active electrode filled with a suitable ionic drug solution so that when an electric field is established during the iontophoresis application, ions of the drug solution will migrate from the drug reservoir into a bloodstream of a patient. But, in the past, the filling of the reservoir adversely required complete removal of the release liner in order to expose the fluid reservoir since there was never before, as taught herein, a convenient access window available. Consequently, the prior art application techniques prematurely exposed their adhesive layer and denigrated the adhesive properties thereof.

In stark contrast, now with reference to FIGS. 1 and 4, a typical iontophoretic application of the bioelectrode 20 in accordance with the present invention is described. In particular, a clinician may fill fluid reservoir 32 by simply opening the access window 42. The opening may be partial or fall depending upon how far the clinician bends back the access window 42. It should be apparent, however, that while the clinician has a filling access to the fluid reservoir, the adhesive layer 28 remains completely and totally covered by the portion of the release liner 38 that is not cut out as part of the access window 42. This in turn prevents premature exposure of the adhesive layer 28 and the all the aforementioned problems associated therewith. Yet access to the expanse of the reservoir allows rapid and complete filling thereof.

After the particular fluid reservoir is at least partially filled and the clinician has readied the bioelectrode 20 and the patient tissue area for use, the clinician simply removes the release liner 38 by peeling away the release liner 38 from the adhesive layer 28 and secures the bioelectrode 20, by way of the adhesive layer 28, to the patient's skin. Again, removal of the release liner 38 may be facilitated by utilizing the peel tab 40 in a pulling fashion well known to those skilled in the art.

Figure 5:
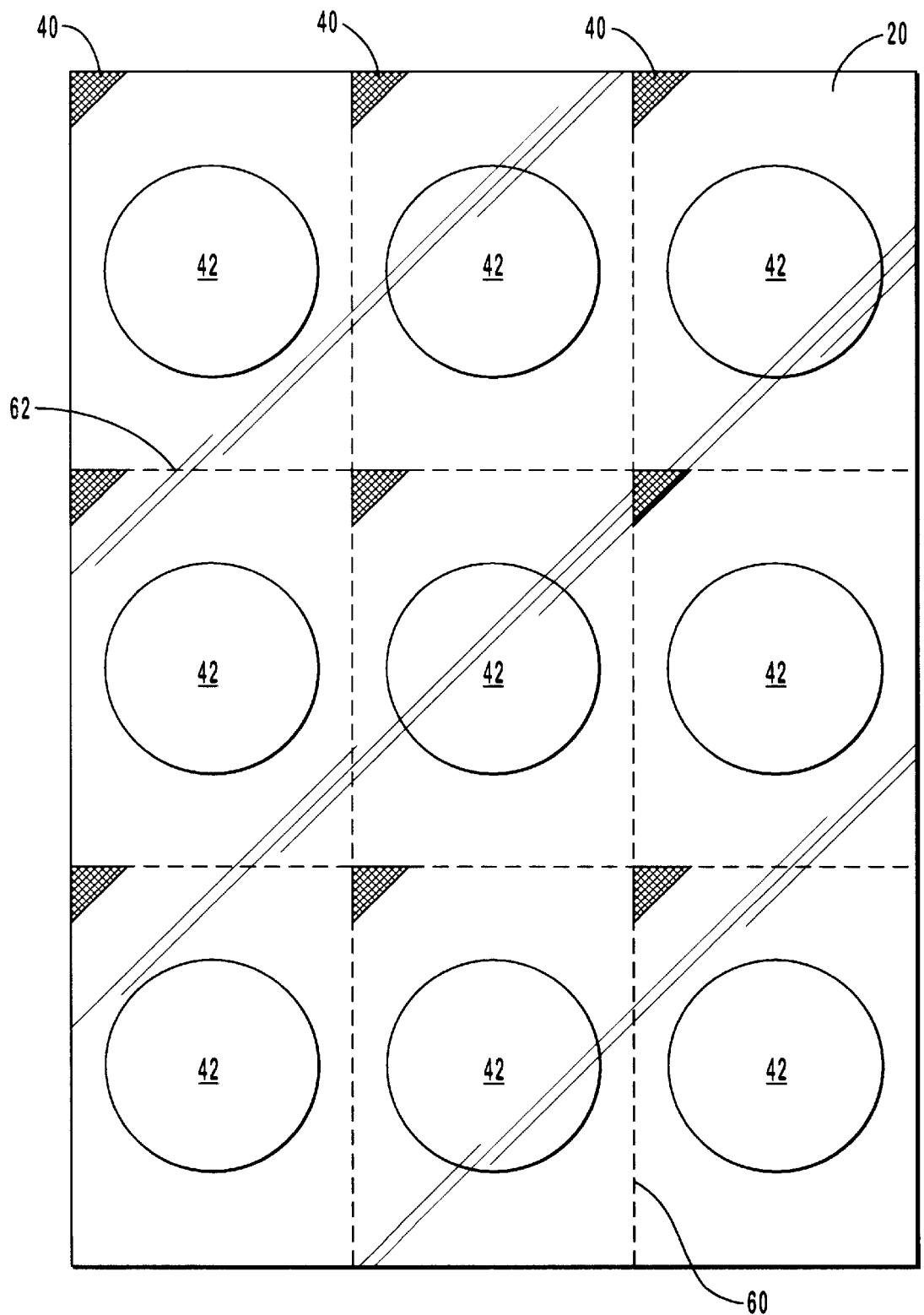
FIG. 5 is a top side, partial plan view of a plurality of bioelectrodes according to a further alternate embodiment of the present invention.

Finally, reference now to FIG. 5, a palette 58 may be desired in order to manufacture a plurality of bioelectrodes 20 similar to the individual bioelectrodes 20 previously described. The palette 58 may also be for fluid reservoirs 32 having rectangular or circular shapes and correspondingly shaped access windows 42. Peel tabs 40 are again useful in order to facilitate removal of an individual bioelectrode 20. It is contemplated that removal means may be provided such as by horizontal 60 and vertical 62 perforations in the palette 58 or by other means such as pre-pressed folds.

The present invention may also be embodied in other specific forms without departing from its spirit or essential characteristics and, again, the described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A hydratable bioelectrode configured for delivering ions of an ionic solution comprising:
 a reservoir capable of receiving an ionic solution;
 a conductive element associated with said reservoir, said conductive element being (i) adapted for connection to a source of electrical current, and (ii) disposed so as to transfer said current through said conductive element in order to deliver said ions;
 an adhesive layer cooperatively mounted about said reservoir in order to secure said bioelectrode to a patient during use;
 a release liner covering said adhesive layer and said reservoir in order to protect said adhesive layer and said reservoir until said bioelectrode is readied for use; and
 an access window defined on a portion of said release liner covering said reservoir so that during preparation of said bioelectrode for use, said reservoir can be at least partially exposed by opening said access window, thereby allowing said reservoir to receive said solution without exposing said adhesive layer.

2. A bioelectrode according to claim 1, wherein said access window defined on said portion of said release liner is a partial cutout of said release liner.

3. A bioelectrode according to claim 2, wherein said partial cutout is one of a substantially circular and substantially rectangular shape.

4. A bioelectrode according to claim 1, further comprising a means to facilitate connection of said conductive element to said source of electrical current.

5. A bioelectrode according to claim 1, wherein said adhesive layer is a portion of a substrate.

6. A palette having a plurality of hydratable bioelectrodes configured thereon, each said bioelectrode being configured for delivering ions of an ionic solution, each said bioelectrode comprising:
 a reservoir capable of receiving said solution;
 a conductive element associated with said reservoir, said conductive element being (i) adapted for connection to a source of electrical current, and (ii) disposed so as to transfer said current through said conductive element in order to deliver said ions;
 an adhesive layer cooperatively mounted about said reservoir in order to secure said bioelectrode to a patient during use;
 a release liner covering said adhesive layer and said reservoir in order to protect said adhesive layer and said reservoir until said bioelectrode is readied for use; and
 an access window defined on a portion of said release liner that is covering said reservoir so that during preparation of said bioelectrode for use, said reservoir can be at least partially exposed by opening said access window, thereby allowing said reservoir to receive said solution without exposing said adhesive layer.

7. A palette according to claim 6, further comprising a means for individually separating each said bioelectrode from said palette.

8. A palette according to claim 7, wherein said means for separating comprises a perforated edge between each said bioelectrode.

9. A palette according to claim 6, wherein each said access window defined on said portion of said release liner is a partial cutout of said release liner.

10. A bioelectrode according to claim 9, wherein said partial cutout is one of a substantially circular and substantially rectangular shape.

11. A palette according to claim 6, further comprising a peel tab for each said bioelectrode in order to facilitate removal of said release liner during use of said bioelectrode.

12. In a hydratable bioelectrode configured for delivering ions of an ionic solution having a reservoir for receiving said solution, a conductive element associated therewith, an adhesive layer mounted about said reservoir, a release liner covering both said adhesive layer and said reservoir, and an access window defined on a portion of said release liner covering said reservoir, a method of using said bioelectrode, comprising the steps of:

at least partially opening said access window without exposing said adhesive layer in order to reveal said reservoir;

at least partially filling said reservoir with said solution.

13. A method according to claim 12, further comprising the steps of:

peeling away said release liner in order to expose both said adhesive layer and said reservoir; and securing said bioelectrode to a patient by adhering said adhesive layer onto an exposed tissue surface.

14. A method according to claim 13, wherein said solution is a drug solution, further comprising the step of:

securing another bioelectrode onto said surface;

creating a flow of electrical current between said bioelectrode and said another bioelectrode in order that said ions might migrate from said reservoir into a bloodstream of said patient.

15. A method according to claim 14, wherein said step of creating an electrical current further comprises the step of:

attaching a suitable power source across said bioelectrode and said another bioelectrode.

\* \* \* \* \*